United States Patent [19]
Kotitschke et al.

[11] Patent Number: 5,099,003
[45] Date of Patent: Mar. 24, 1992

[54] METHOD OF PREPARING A STERILE PLASMA-PROTEIN SOLUTION CONTAINING FIBRINOGEN AND FACTOR XIII

[75] Inventors: Ronald Kotitschke, Dreieich; Axel W. Stemberger, Neubiberg; Wolfgang Stephan, Dreieich, all of Fed. Rep. of Germany

[73] Assignee: Biotest Pharma GmbH, Dreieich, Fed. Rep. of Germany

[21] Appl. No.: 256,531

[22] Filed: Oct. 12, 1988

[30] Foreign Application Priority Data

Oct. 15, 1987 [DE] Fed. Rep. of Germany ....... 3734923

[51] Int. Cl.⁵ .................. C07K 15/14; C07K 3/24; C07K 3/22; C07K 3/28
[52] U.S. Cl. .................................. 530/382; 530/380; 530/383; 530/384; 530/419; 530/416
[58] Field of Search ............... 530/383, 380, 384, 382, 530/419, 416

[56] References Cited

U.S. PATENT DOCUMENTS

| | | | |
|---|---|---|---|
| 4,170,590 | 10/1979 | Stephan et al. | 530/382 |
| 4,435,318 | 3/1984 | Pabst et al. | 530/383 |
| 4,597,899 | 7/1986 | Falke | 530/383 |
| 4,600,574 | 7/1986 | Lindner et al. | 424/28 |
| 4,627,879 | 12/1986 | Rose et al. | 106/124 |
| 4,650,678 | 3/1987 | Fuhge et al. | 424/101 |
| 4,816,251 | 3/1989 | Seelich | 424/101 |
| 4,822,872 | 4/1989 | Kameyama et al. | 530/383 |

OTHER PUBLICATIONS

Abstract from World Patent Index (Dialog file 351), Accession No. 81-93336D/51 of Gautam, M.
Abstract from Biotechnology Abstracts (Dialog file 357), Accession No. 83-00627.
Kotitschke et al. 1980, *Protide and Biological Fluids*, Peeters, H. (ed.), 28 Collequium, Oxford, N.Y., Pergamon Press, pp. 333-337.

*Primary Examiner*—Margaret Moskowitz
*Assistant Examiner*—Keith C. Furman
*Attorney, Agent, or Firm*—Sprung Horn Kramer & Woods

[57] ABSTRACT

A method of preparing a sterile and stable plasma-protein solution containing fibrinogen and Factor XIII from human blood plasma which has been stabilized with citrate, comprising treating the plasma with β-propiolactone and irradiating it with ultraviolet light, removing the Factors II, VII, IX and X by adsorption onto anion exchangers that adsorb proteins, precipitating the companion proteins out by adding ethanol until the solution has a final concentration of about 9% by volume at $-3°$ C., centrifuging the precipitate off, dissolving the precipitate in a citrate buffer at a pH of about 6.35 and a temperature of about 37° C., adjusting the protein level of the solution to about 13.3 g/l with sodium citrate solution, adding ethanol, a glycine citrate buffer, and a solution of sodium citrate to precipitate out the companion proteins, adding ethanol to the remaining solution until the solution has a final concentration of about 9% by volume at $-3°$ C., thereby precipitating fribrinogen and Factor XIII, dissolving the precipitate in a citrate buffer at a pH of about 6.35 and a temperature of about 37° C., and filtering the solution.

5 Claims, 1 Drawing Sheet

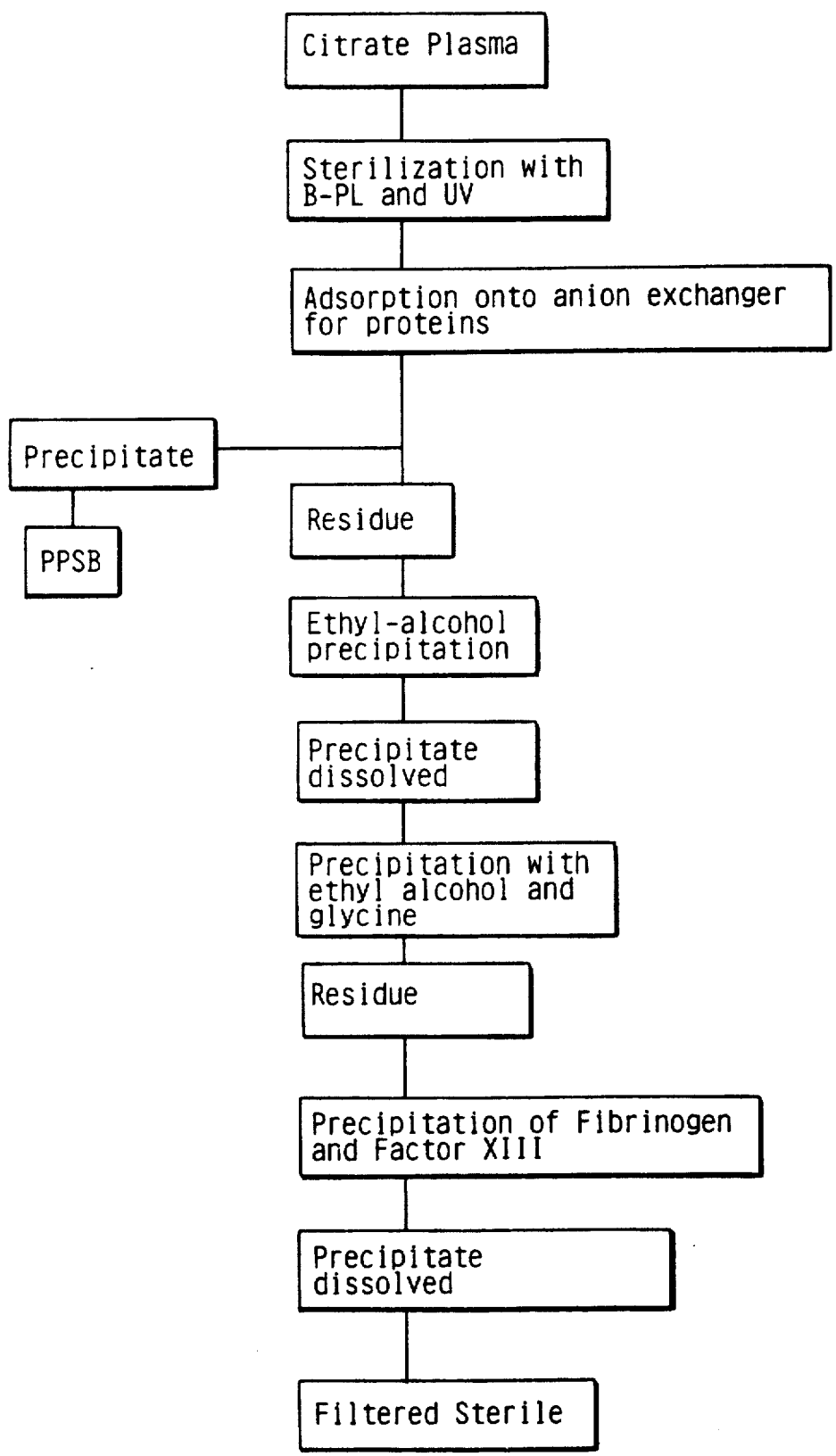

METHOD OF PREPARING A STERILE PLASMA-PROTEIN SOLUTION CONTAINING FIBRINOGEN AND FACTOR XIII

The invention relates to a method of preparing a sterile plasma-protein solution containing fibrinogen and Factor XIII and especially appropriate as a constituent of a fibrin adhesive, from human blood plasma stabilized with citrate.

A number of different methods of preparing fibrinogen from plasmas are known from the literature. Most of them employ the ethanol precipitation described by Cohn (Journal of the American Society 72 [1950], 564–474). One known further development has been described by Blombäck et al.(Archiv für Kemi 10 [1956], 29, 415–43).

Blood-plasma fractions are very likely to be infectious. They entail in particular the hazard of transmitting hepatitis B virus and hepatitis non-A/non-B virus and now human immunodeficiency virus (HIV).

Fibrinogen and the Cohn I fraction are among what are considered high-risk preparations in terms of the risk of hepatitis (J.F. Hoofnagel et al, J. Lab. Clin. Med. 88 [1976], 102 and W. Doleschel et al, Wiener Klin. Wschr. 89 [1977], 383).

The clinical use of fibrinogen preparations collected from large plasma pools is accordingly prohibited in the USA.

Since it is impossible to use diagnostic measures to prepare hepatitis-safe blood products from plasma pools, various methods of sterilizing blood constituents have been developed. Pasteurization (for 10 hours at 60° C.) has been employed successfully with albumin and was described several years ago in conjunction with stabilizers such as amino acids and monosaccharides and oligosaccharides and sugar alcohol to sterilize such sensitive plasma proteins as Factors II, VIII, and XIII (EP-B 0 018 561). The effectiveness of pasteurization in the presence of these stabilizers has not been determined and is now being tested.

G.A. LoGrippo with H. Hayashi (Henry Ford Hosp. Med. J. 21 [1973], 181) and with F.W. Hartmann (Bibl. Haematol. 7 [1958], 225) has described a method of cold sterilization that combines treating human blood plasma with 8-propiolactone and ultraviolet radiation.

Sterilizing an already purified fibrinogen fraction with 8-propiolactone and ultraviolet radiation results in fibrinogen products that will no longer coagulate (R. Kotitschke & W. Stephan, Proteins and Related Subjects, Vol. 28, Protides of Biological Fluids, Peeters H., 28th Colloquium, 1980, Oxford, New York, Toronto, and Paris, Pergamon Press, 333-37; H. Brunner et al., Verhandlungen der Deutsch. Gesellsch. for Inn. Med. 79 [1983], 1130–34; and W. Doleschel & W. Auerswald, Pharmacology 2 [1969], 1).

EP-B 0 014 333 describes a method of preparing the plasma fractions, fibrinogen, a prothrombin complex containing Factors II, VII, IX, and X, antithrombin III, and a solution of storage-stable serum proteins from a plasma stabilized with citrate and treated with 8-propiolactone and ultraviolet radiation. The fibrinogen is in this process prepared from a pool of citrate plasma treated with $\beta$-propiolactone and irradiated with ultraviolet by adsorption onto colloidal silicic acid followed by elution. This fibrinogen is not appropriate as a constituent of a fibrin adhesive because a fibrinogen of that type contains no Factor XIII. For a fibrinogen preparation to satisfy the prerequisites of being used in an adhesive it must be enriched with concentrated Factor XIII.

The separate fibrin polymers in the biological fibrin-adhesive system are crosslinked by Factor XIII that has been activated by calcium ions and thrombin, resulting in an insoluble, solid, and elastic fibrin clot (H.P. Spängler & F. Braun, Grundlagen der Fibrinklebung in der operative Medizin, Deerfield Beach, Florida and Basel, Edition Medizin. Weinheim, 1983).

The significance of the Factor XIII content of the fibrin-adhesive system has been demonstrated in in-vivo skin-bonding tests (H.P. Spängler et al, Wien. Klin. Wochenschr. 85 [1973], 827).

Since methods of preparing sterile Factor XIII concentrates from human plasma are very expensive, they are preferably prepared from human placentas (Canadian Patent 957 943). Winkelman et al (Thrombosis and Haemostasis 55 [1986], 3, 402–05) describe the preparation of concentrated Factor XIII from plasma from which the cryoprecipitate has been removed. Solutions that contain human Factor XIII must be sterilized to prevent the transmission of viruses (EP-B 0 037 078).

The object of the present invention is to prepare from human plasma a sterile and stable plasma-protein solution containing both Factor XIII and fibrinogen, that is concentrated in relation to the plasma, and that is especially appropriate as a constituent of a fibrin adhesive.

This object is attained in accordance with the invention in that the plasma that has been stabilized with citrate is treated with $\beta$-propiolactone and irradiated with ultraviolet light, the Factors II, VII, IX and X are removed by adsorption onto anion exchangers that adsorb proteins, the companion proteins are precipitated out with ethanol until the solution has a concentration of 9% by volume at $-3°$ C., the precipitate is centrifuged out and dissolved while being stirred in a citrate buffer at a pH of 6.35 and a temperature of 37° C., the protein level of the fibrinogen solution is adjusted to 13.3 g/l with sodium citrate solution, further companion proteins are precipitated out with ethanol, a glycine citrate buffer, and a solution of sodium citrate, the precipitate is centrifuged out, the fibrinogen and Factor XIII are precipitated from the residue by adding ethanol until the solution has a concentration of 9% by volume at $-3°$ C., the precipitate is dissolved, while being stirred, to the desired concentration of fibrinogen in a citrate buffer at a pH of 6.35 and a temperature of 37° C, and the solution is filtered through a filter-clarification disk and a millipore sterile filter.

The plasma is treated with B-propiolactone at a range of concentrations of 0.2 to 0.35% by volume of the starting plasma and at a pH of 7.2. The ultraviolet dose is $4\times20$ watts 1 cm away from a layer of plasma 0.15 mm thick flowing at a rate of 2 l/h and with the ultraviolet tube rotating at 700 rpm.

If a plasma that has been treated with $\beta$-propiolactone and ultraviolet radiation is fractionated in this way without the Factors II, VII, IX and X having been separated, the resulting fraction will contain unstable fibrinogen and Factor XIII, meaning that the products will gel and clot, making further processing impossible.

The method in accordance with the invention provides, from human blood plasma that has been stabilized with citrate, a high-clotting, hepatitis-safe, and therapeutically usable solution of plasma protein that contains the fibrinogen and Factor XIII in a form that is enriched in relation to the starting plasma. This solution is especially appropriate as a constituent of a fibrinogen adhesive.

The following table illustrates the properties of two plasma-protein solutions prepared by the method in accordance with the invention and with protein concentrations that differ in accordance with the purposes for which they are to be employed.

TABLE

| Protein (g/l) | Fibrinogen (g/l) | Factor XIII (U/ml) |
|---|---|---|
| 60 | 50 | 6 |
| 90 | 75 | 9 |

The invention will now be described more specifically in the following illustrative example.

EXAMPLE

Sixty blood-plasma bags of fresh-frozen citrate plasma weighing a total of 37.2 kg were allowed to stand overnight at +8° C. The bags were then opened with a scalpel under laminar flow and the frozen plasma thawed in a boiler with a heating jacket at 37° C by being stirred.

The plasma pool was cooled for approximately 45 minutes to approximately 10° C. 92.5 ml of β-propiolactone (0.25%) dripped into the plasma while it was being stirred. Once the pH was 7.2, it was maintained constant by adding 1 N sodium hydroxide for 1 hour at room temperature, consuming 1 l of the hydroxide. A 0.15-mm thick layer of the propiolactone-treated plasma flowing at a rate of 2 l/h was subjected to 4×20 watts of ultraviolet radiation from 1 cm away with the ultraviolet tube rotating at 700 rpm.

1.5 g of DEAE SEPHADEX A 50 was employed per kg of plasma to adsorb the PPSB factors. The batch was allowed to rest for 1 hour, and the Sephadex precipitated out overnight. The plasma was removed from over the sediment the next day with a riser and a pump.

The pH was adjusted to 7.2 and the plasma chilled to 0° C. 96% ethanol was added while the plasma was being stirred until the concentration was 9%. The temperature was decreased to −3° C. Precipitation continued for 14 hours. The precipitate was centrifuged at −15° C. at 1 l/min and 211 000 rpm in an angled-head centrifuge.

The precipitated plasma-protein fraction (350 g of precipitate) was dissolved in 1200 ml of a citrate buffer at a pH of 6.35 and a temperature of +37° C for 45 minutes while being stirred.

The protein level was adjusted to 13.3 g/l with a sodium citrate solution (0.055 M) at a pH of 6.35. The companion proteins were precipitated out with 240 ml of glycine citrate buffer, 260 ml of ethanol, and 1500 ml of citrate solution per kg of fibrinogen solution. Subsequent to approximately 1 hour of precipitation the precipitate was centrifuged off and the fibrinogen and Factor XIII precipitated out of the residue by adding ethanol until the concentration was 9% at −3° C. The precipitate was diluted to the desired fibrinogen concentration with a solution buffer at +37° C. by being stirred.

The fibrinogen solution was initially filtered through a filter-clarification disk and then over a millipore sterilizing filter. The sterile-filtered solution was deepfrozen at −80° C. for further use.

The drawing is a flow chart of the method in accordance with the invention.

It will be understood that the specification and examples are illustrative but not limitative of the present invention and that other embodiments within the spirit and scope of the invention will suggest themselves to those skilled in the art.

We claim:

1. A method of preparing a sterile plasma-protein solution containing fibrinogen and Factor XIII from human blood plasma which has been stabilized with citrate, comprising
a) treating the plasma with βpropiolactone and irradiating it with ultraviolet light,
b) removing the Factors II, VII, IX and X by adsorption onto anion exchangers that adsorb proteins,
c) precipitating fibrinogen, Factor XIII and other proteins by adding ethanol until the solution has a concentration of about 9% by volume at −3° C.,
d) centrifuging off the precipitate of step (c),
e) dissolving such precipitate in a citrate buffer at a pH of about 6.335 and a temperature of 37° C.,
f) adjusting the protein level of the solution to 13.3 g/l with sodium citrate solution,
g) adding ethanol, a glycine citrate buffer, and a solution of sodium citrate to precipitate out companion proteins other than fibrinogen and Factor XIII,
h) adding ethanol to the remaining solution until the solution has a concentration of about 9% by volume at −3° C., thereby precipitating fibrinogen and Factor XIII,
i) dissolving the precipitate from step (h) in a citrate buffer at a pH of about 6.35 and a temperature of about 37° C., and
j) filtering the solution.

2. The method according to claim 1, wherein in step (a) the treatment with βpropiolactone is carried out at a range of concentration of about 0.2 to 0.35% by volume of the starting plasma and at a pH of about 7.2.

3. The method according to claim 1, wherein in step (b) the protein-adsorbing anion exchangers are cross-linked dextrans or celluloses with diethylaminoethyl groups and are employed in proportions of about 0.5 to 3 g per kg of plasma.

4. The method according to claim 1, wherein in step (g) the companion proteins are precipitated from 1 kg of fibrinogen solution with about 260 ml of ethanol, 240 ml of glycine citrate buffer, and 1500 ml of sodium citrate solution.

5. The method according to claim 1, wherein in step (i) the fibrinogen is finally dissolved to a concentration in the range of about 40 to 80 g/l.

* * * * *

UNITED STATES PATENT AND TRADEMARK OFFICE
CERTIFICATE OF CORRECTION

PATENT NO. : 5,099,003

DATED : March 24, 1992

INVENTOR(S) : Kotitschke et al.

It is certified that error appears in the above-identified patent and that said Letters Patent is hereby corrected as shown below:

Title Page   OTHER PUBLICATIONS:  Insert -- Pamphlet on " Ion Exchange Chromatography: , Pharmacia Fine Chemicals AB, PP 4-17, and 66-67. --

Col. 4, line 29   Delete " 6.335 " and substitute -- 6.35 --

Signed and Sealed this

Thirteenth Day of July, 1993

Attest:

MICHAEL K. KIRK

Attesting Officer

Acting Commissioner of Patents and Trademarks